US008557257B2

(12) United States Patent
Morton

(10) Patent No.: US 8,557,257 B2
(45) Date of Patent: Oct. 15, 2013

(54) MYCOBACTERIAL IMMUNOTHERAPY FOR CANCER TREATMENT

(75) Inventor: Donald L. Morton, Pacific Palisades, CA (US)

(73) Assignee: Oncovac Inc., Pacific Palisades, CA (US)

( * ) Notice: Subject to any disclaimer, the term of this patent is extended or adjusted under 35 U.S.C. 154(b) by 625 days.

(21) Appl. No.: 12/293,766

(22) PCT Filed: Mar. 23, 2007

(86) PCT No.: PCT/US2007/064815
§ 371 (c)(1),
(2), (4) Date: Jun. 15, 2010

(87) PCT Pub. No.: WO2007/112316
PCT Pub. Date: Oct. 4, 2007

(65) Prior Publication Data
US 2010/0247440 A1    Sep. 30, 2010

Related U.S. Application Data

(60) Provisional application No. 60/785,832, filed on Mar. 24, 2006.

(51) Int. Cl.
*A61K 49/00*    (2006.01)
*A61K 39/02*    (2006.01)
*A61K 39/04*    (2006.01)

(52) U.S. Cl.
USPC ......... 424/248.1; 424/9.1; 424/92; 424/234.1

(58) Field of Classification Search
USPC .............................. 424/9.1, 9.2, 234.1, 248.1
See application file for complete search history.

(56) References Cited

U.S. PATENT DOCUMENTS

| | | | |
|---|---|---|---|
| 5,700,649 A | 12/1997 | Morton et al. | 435/7.1 |
| 5,840,317 A | 11/1998 | Morton | 424/184.1 |
| 5,882,654 A | 3/1999 | Morton | 424/277.1 |
| 5,993,828 A | 11/1999 | Morton | 424/277.1 |
| 6,090,385 A | 7/2000 | Maes | 424/179.11 |
| 6,168,787 B1 | 1/2001 | Morton | 424/93.21 |
| 2003/0138436 A1* | 7/2003 | Le Gros et al. | 424/184.1 |

FOREIGN PATENT DOCUMENTS

WO    WO 95/26742    10/1995
WO    WO 2006/122380    11/2006

OTHER PUBLICATIONS

Habal, N., et al. Annals of Surgical Oncology, vol. 7, No. 5, pp. 352-356, 2000.*
Gupta, R.K, et al. Clinical and Applied Immunology Reviews, vol. 4, pp. 395-410, 2004.*
Bluming, A.Z., et al. Annals of Internal Medicine, vol. 76, pp. 405-411, 1972.*
Nathanson, L., et al. Cancer, vol. 43, pp. 1630-1635, 1979.*
Alexandroff et al., "BCG immunotherapy of bladder cancer: 20 years on," The Lancet, 353 1689-1694, 1999.
Allred et al., "Comprehensive evaluation of prognostic factors by immunocytochemistry on extremely small samples (50mg) of 'pulverized' breast carcinomas," Breast Cancer Res. Treat., 16: 182 (149), 1990, (abstract only).
Agarwala et al., "Mature results of a phase III randomized trial of bacillus Calmette-Guerin (BCG) versus observation and BCG plus dacarbazine versus BCG in the adjuvant therapy of American Joint Committee on Cancer Stage I-III melanoma (E1673): a trial of the Eastern Oncology Group," Cancer, 100 (8): 1692-1698, 2004.
Böhle, "Recent knowledge on BCG's mechanism of action in the treatment of superficial bladdaer cancer," Brazilian J. of Urology, 26 (5): 488-502, 2000.
Czarnetzki et al., "Long-term adjuvant immunotherapy in stage I high risk malignant melanoma, comparing two BCG preparations versus non-treatment in a randomised multicentre study (EORTC Protocol 18781)," Eur. J. Cancer, 29A(9): 1237-1242, 1993.
Doolittle and Ben-Zeev, "Immunodetection of lipoprotein lipase: antibody production, immunoprecipitation, and western blotting techniques," Methods and Mol. Biol., 109: 215-237, 1999.
Habal et al., "CancerVax, an allogeneic tumor cell vaccine, induces specific humoral and cellular immune responses in advanced colon cancer," Annals of Surgical Oncology, 8 (5): 389-401, 2001.
Henz et al., "Prognostic value of tuberculin and BCG immunoreactivity in stage I high-risk malignant melanoma (EORTC protocol 18781)," 193 (2): 105-109, 1996.
Hseuh et al., "Prolonged survival after complete resection of disseminated melanoma and active immunotherapy with a therapeutic cancer vaccine," J. of Clinical Oncology, 20 (23):4549-4554, 2002.
Hsueh et al., "Active immunotherapy by reinduction with a polyvalent allogeneic cell vaccine correlates with improved survival in recurrent metastatic melanoma," Annals of Surgical Oncology, 9 (5): 486-492, 2002.
International Search Report and Written Opinion, issued in Int. App. No. PCT/US2007/64815, mailed Mar. 11, 2008.
Jones et al., "Immune response to polyvalent melanoma cell vaccine in AJCC stage III melanoma: an immunologic survival model," Annals of Surgical Oncology, 3 (5): 437-445, 1996. (Abstract only).
Kavanagh et al., "Adjuvant therapies in the treatment of Stage II and III malignant melanoma," Surgeon, 3(4): 245-256, 2005.
Kelley et al., "Tumor-associated antigen TA90 immune complex assay predicts recurrence and survival after surgical treatment of stage I-III melanoma," J. of Clinical Oncology, 19 (4): 117-1182, 2001.
Lamm et al., "Randomized intergroup comparison of cacillus calmette-guérin immunotherapy and mitomycin C chemotherapy prophylaxis in superficial transitional cell carcinoma of the bladder," Urol. Oncol., 1: 119-126, 1995.

(Continued)

Primary Examiner — Rodney P. Swartz
(74) Attorney, Agent, or Firm — Parker Highlander PLLC

(57) ABSTRACT

Methods of Mycobacterial immunotherapy for the treatment of cancer are described. In certain cases, these methods concern administration of attenuated Mycobacteria by intradermal injection into non tumor tissues. Methods of the invention, provide safe and effective treatments for malignant tumors and the compositions for use in such treatments. Methods for determine the effectiveness of such immunotherapies are also described.

19 Claims, 7 Drawing Sheets

(56) References Cited

OTHER PUBLICATIONS

Lipton et al., "*Corynebacterium parvum* versus bacille calmette-guerin adjuvant immunotherapy of stage II malignant melanoma," *J Clin. Oncol.*, 9 (7): 1151-1156, 1991.

McLean et al., "A randomized study of methanol-extraction residue of bacille calmette-guerin as postsurgical adjuvant therapy of uveal melanoma," *Am. J. Ophthalmol.*, 110 (5): 522-526, 1990.

Mitchell, "Combining chemotherapy with biological response modifiers in treatment of cancer," *J. Nat. Cancer Inst.*, 80: 1445-1450, 1998.

Morton et al., "BCG immunotherapy as a systemic adjunct to surgery in malignant melanoma," *Medical Clinics of North America*, 60 (3): 431-439, 1976.

Morton et al,. "BCG immunotherapy of malignant melanoma: summary of a seven-year experience," *Ann. Surg.*, 180 (4): 635-643, 1974.

Morton et al., "BCG immunotherapy of melanoma: results of a clinical trial," *BCG in Cancer Immunotherapy*, 209-214.

Morton et al., "Immunological factors which influence response to immunotherapy in malignant melanoma," *Surgery*, 68 (1): 158-164, 1970.

Organon Canada Ltd., OncoTICE [Bacillus calmotte-gurin (BCG), Strain TICE] Antineoplastic agent for bladder instillation, 9,2001.

Remington's Pharmaceutical Sciences. 18th Ed, Mack Printing Company, 1990.

Silver et al., "Adjuvant BCG immunotherapy for stage I and II malignant melanoma," *Can. Med. Assoc. J.*, 128: 1291-1295, 1983.

Tan and Ho, "Pooled analysis of the efficacy of bacille calmette-guerin (BCG) immunotherapy in malignant melanoma," *J. Dermatol. Surg. Oncol.*, 19 (11): 985-990, 1993.

Uyl-de Groot et al., "Immunotherapy with autologous tumor cell-BCG vaccine in patients with colon cancer: a prospective study of medical and economic benefits," *Vaccine*, 23: 2379-2387, 2005.

Witjes et al., "A randomised prospective study comparing intravesical instillations of mitomycin-C, BCG-Tice, and BCG-RIVM in pTa-pT1 tumours and primary carcinoma in situ of the urinary bladder, Dutch South-East Cooperative Urological Group," *Eur. J. Cancer*, 29A (12): 1672-1676, 1993.

Zbar et al., "The immunity produced by the intradermal inoculation of living tumor cells and living *Mycobacterium bovis* (Strain BCG(," *Science*, 170 (3963): 1217-1218, 1970. (abstract only).

European Search Report, issued in European Application No. 07759274.9, mailed May 7, 2010.

Hadjiev et al., "The effect of BCG treatment of gastric carcinoma—three case reports," *Folia Medica*, 23:59-65, 1981.

Hadjiev et al., "The effect of dosage and treatment scheme on results from treatment of lung cancer with BCG and F70," *Folia Medica*, 25:8-15, 1983.

\* cited by examiner

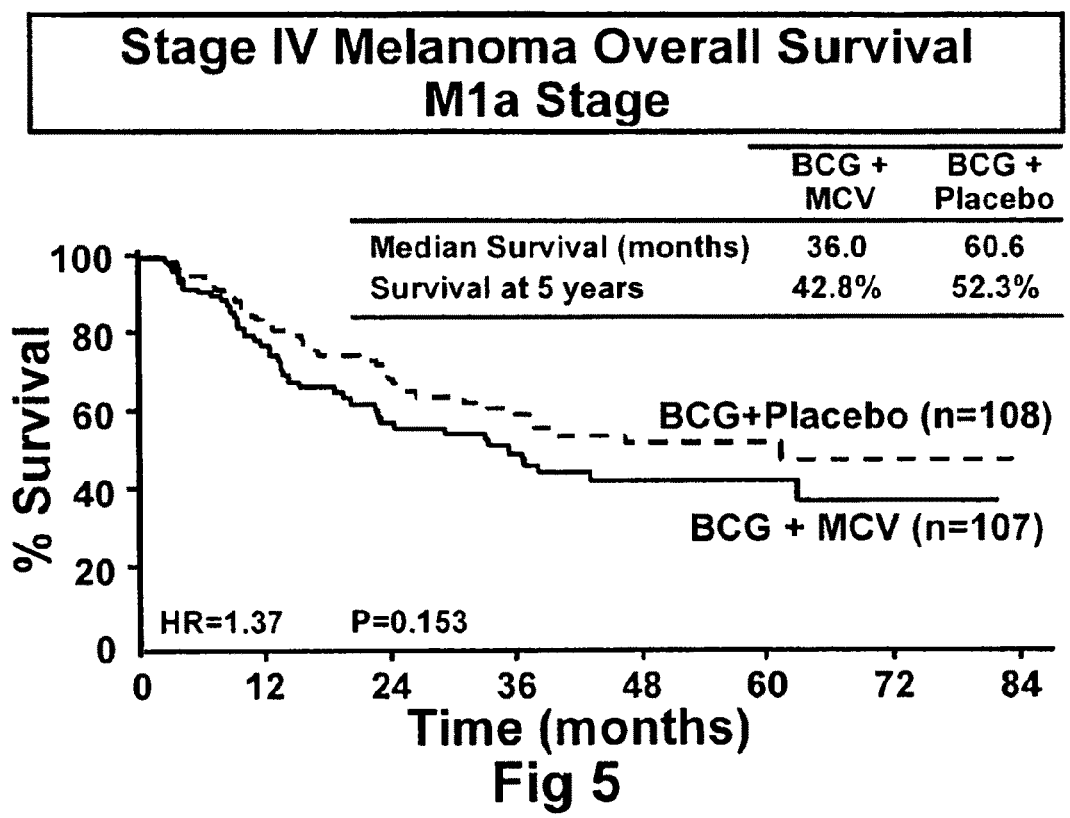

Stage IV M1a Stage Following Complete Resection of M1a Melanoma: Selected Series

- Median survival: 21 months
- 5-year survival rates: mean 21%

| Study | Site of Metastasis | N | Median Survival (mos) | 5-Yr OS (%) |
|---|---|---|---|---|
| Gadd | Solitary lesion M1a (all) | 190 | 18.5 | 14 |
| Karakousis | Distant lymph nodes | 23 | 29 | 22 |
|  | Subcutaneous | 27 | 24 | 33 |
| Barth | M1a (all) | 281 | 15 | 14 |
| Meyer | Distant lymph nodes | 45 | 18 | 20 |
|  | Skin/subcutis | 30 | 17 | 17.8 |

Literature Series     Median    <u>21 mos</u>    5 Yr OS   <u>21 %</u>

BCG+Placebo   M1A   Median   <u>60.6 mos</u>    5 Yr OS   <u>52.3%</u>

Fig 6

MYCOBACTERIAL IMMUNOTHERAPY FOR CANCER TREATMENT

This application is a national phase application under 35 U.S.C. §371 of International Application No. PCT/US2007/064815 filed Mar. 23, 2007, which claims the benefit of U.S. Provisional Patent Application No. 60/785,832, filed on Mar. 24, 2006.

The United States Government has certain rights to this invention pursuant to grant no. CA12582 from the National Institutes of Health.

BACKGROUND OF THE INVENTION

1. Field of the Invention

The present invention concerns the field of cancer therapy. Specifically, the invention concerns methods for treating malignant tumors by administration of attenuated Mycobacterial compositions.

2. Description of Related Art

A long sought goal in cancer therapy has been the development of safe and effective immunotherapeutic agents that can stimulation a patient's immune system to attack cancer cells. A variety of approaches have been tested in this regard with little success. For example, compositions of inactivated cancer cells have been tested as potential cancer vaccines (U.S. Pat. Nos. 6,168,787; 5,882,654 and 5,840,317). Another method for immunotherapy that has been extensively evaluated is the administration of attenuated bacterial pathogens. In particular a number of studies have evaluated the administration of attenuated Mycobacteria for cancer immunotherapy. Mycobacteria are the causative agents of infectious diseases such tuberculosis and even attenuated strains are known to illicit a strong humoral and cell mediated immune response. In particular, a number of studies have evaluated the immunotherapeutic potential of various sub-strains of attenuated bacille Calmette and Guerin (BCG) *Mycobacterium bovis* (Grange et al., 1983). Unfortunately, immunotherapies with such attenuated bacteria have only been effective in certain very specific cases.

It has been previously demonstrated that intratumoral injection of live BCG can mediate tumor regression of intradermal metastases (Morton et al., 1970; Pardridge et al., 1979). Studies comparing this technique to administration of BCG to non-tumor tissue by standard tine technique or heat perfusion indicated that intratumoral administration was the superior treatment (Morton et al., 1976). However, live BCG has also been installed intravesically for the treatment and prevention of recurrence for some types of bladder cancer. In this case anywhere from 1 to $8 \times 10^8$ colony forming units are administered into the bladder per dosage (Witjes et al., 1993; Lamm et al., 1995). However, both of these treatment methods can potentially result in systemic introduction of bacteria. Because cancer therapies are often used in conjunction with surgical approaches such as full or partial tumor resection, local administration of BCG typically can not immediately follow surgical resections.

Despite the efficacy of Mycobacterial immunotherapy in these certain specific cases wherein the bacteria is administered directly to the tumor little efficacy has been demonstrated when such compositions are administered to sites other then the tumor itself. Since it is preferable, when possible, to surgically remove cancer tissue it would be a highly beneficial to develop a method of delivering Mycobacterial immunotherapy compositions to non-tumor tissue as a post surgical adjuvant to prevent recurrence. However, even using a variety of BCG sub-strains and treatment schedules, Mycobacterial immunotherapy at such sites has failed to show significant protective or anticancer efficacy (Agarwala et al., 2004; Czarnetzki et al., 1993). Additionally, a large randomized trial of BCG in combination with either surgery or chemotherapy failed to show any significant disease free or overall survival benefit attributable to the immunotherapy (Veronesi et al., 1982). Interestingly, these trials each used a very superficial method for administering the attenuated bacteria. For example, Veronesi et al., (1982) delivered BCG via HEAT gun needles. Other groups have used similar techniques such as tine template administration or needle scarification, and have also failed to demonstrate statistically significant protection from tumors such as malignant melanoma (Silver et al., 1983). Thus, to date, there has not been described a clinically effective method of administering Mycobacterial immunotherapy to non-tumor tissue for cancer therapy.

SUMMARY OF THE INVENTION

The present invention overcomes the deficiency in the prior art by providing a safe and effective method for treating and/or preventing cancer by administering an attenuated Mycobacterial composition. Methods according to the present invention concern administration of attenuated Mycobacteria to sites that are not on or in a malignant tumor itself. Rather, the attenuated Mycobacteria are delivered to sites that are adjacent to, or distant from the site of a tumor. Attenuated Mycobacterial compositions of the invention will be essentially free of melanoma cells. As demonstrated herein compositions lacking such cells provide more significantly effective treatments for cancer. Thus, in certain embodiments the invention provides a method for treating a malignant tumor in a subject comprising administering to the subject a therapeutically effective dosage of an attenuated Mycobacterial composition wherein said composition is not administered directly to the tumor and wherein said composition is essentially free of melanoma cells.

As used herein the term "attenuated Mycobacterial" or "attenuated Mycobacteria" refers to a strain of *Mycobacterium* that is not typically pathogenic in a human with an intact immune system. For some applications of the invention, attenuated Mycobacteria comprise live bacteria that are capable of active proliferation. Thus, the dosage of such Mycobacteria may be quantified by the number of live bacteria colonies that can be formed when the bacteria are allowed to proliferate. This quantifiable unit is referred to as a "colony forming unit" or CFU. In some instances however, attenuated *Mycobacterium* can be killed or inactivated bacteria (i.e. heat killed bacteria). It will understood however that compositions of killed bacteria may, in some cases, still be quantified in terms of CFU prior to the killing of the bacteria.

A variety of species and strains of attenuated Mycobacteria may be used in the methods and compositions of the invention. For example, in certain embodiments the attenuated Mycobacteria is attenuated *Mycobacterium bovis*. In certain particular cases the attenuated *Mycobacterium bovis* is the Bacille Calmette-Guerin (BCG) *Mycobacterium bovis*, an attenuated variety that is also used in a vaccine for prevention of Tuberculosis or for treatment of bladder cancer. In very specific embodiments the attenuated Mycobacteria of the invention may be the Tice®, Pasteur or Rijksinstituut voor Volksgezondheid en Milieuhygiene (RIVM) strain of BCG.

In certain preferred embodiments of the invention, attenuated Mycobacterial compositions are administered in relatively low dosages for each treatment. For example in a highly preferred embodiment the attenuated Mycobacteria is administered in a dosage of about $1\times10^4$ to about $5\times10^7$ CFU per treatment. Furthermore, in some specific embodiments the attenuated Mycobacteria is administered in dosage of about $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$ or $1\times10^8$ CFU per treatment, or any range derivable therein. In some very specific instances, attenuated Mycobacteria is administered in dosage range of about $1\times10^5$ to about $5\times10^7$, about $1\times10^5$ to about $1\times10^7$, about $5\times10^5$ to about $5\times10^6$, or about $1\times10^6$ to about $5\times10^6$ CFU per treatment. Thus, it will be understood that in some particular cases the invention provides a method for treating a tumor in a subject comprising administering to the subject a therapeutically effective dosage of an attenuated Mycobacterial composition comprising about $1\times10^4$ to about $1\times10^8$ CFU of Mycobacteria wherein said Mycobacterial composition is not administered directly to the tumor and wherein said composition is essentially free of melanoma cells.

In methods of the instant invention, attenuated Mycobacterial compositions can be administered in a variety of ways. For example in some cases the attenuated Mycobacteria are administered subcutaneously, cutaneously or intradermally. Previous methods of Mycobacteria delivery typically involved tine puncture or needle scarification to deliver the attenuated bacteria into superficial layer of the skin. However, these methods involve spreading the bacteria on the surface of the skin and then making superficial punctures in the epidermis. Such methods that deliver the bacteria to only the uppermost layers of the epidermis have not been found effective in clinical trials. Conversely, in preferred embodiments of the instant invention, attenuated Mycobacteria are administered by direct intradermal injection. Unlike methods used previously, intradermal injection enables delivery of an entire proportion of the attenuated Mycobacterial composition to a layer of the dermis that is accessible to immune surveillance and thus capable of electing an anti cancer immune response and promoting immune cell proliferation at local lymph nodes. Therefore, in some instances that invention provides a method for preventing or treating a tumor in a subject comprising administering to the subject a therapeutically effective dosage of an attenuated Mycobacterial composition wherein said Mycobacterial composition is delivered to non-tumor tissue by intradermal injection and wherein said composition is essentially free of melanoma cells. In certain very specific embodiments, the dosage of attenuated Mycobacteria for administration by such a method is about $1\times10^4$ to about $1\times10^8$ CFU.

As discussed above, methods according to invention involve the delivery of attenuated Mycobacterial compositions to non-tumor tissues. In certain specific embodiments, a dosage of attenuated Mycobacteria may be distributed to two or more sites in the subject. For example, the dosage may be administered at 2, 3, 4, 5, 6, 7, 8, 9, 10 or more sites. Thus, in certain embodiments a dosage of attenuated Mycobacteria is delivered to multiple sites by intradermal injection. It will be understood by one of skill in the art that only a limited volume of the attenuated bacteria can be administered at any one site, since this method of administration generates a "wheal" or pocket of the liquid within the skin. Thus, a particular volume of attenuated Mycobacteria may be distributed to multiple sites, in clusters at one sites or in clusters at multiple sites. In certain cases each wheal will comprise about 0.05 to about 0.3 mls of attenuated Mycobacteria.

In some cases attenuated Mycobacteria is administered to specific sites on or in a subject. For example, the attenuated Mycobacterial compositions according to the invention may be administered adjacent to tumors or adjacent to lymph nodes, such as those that drain tissue surrounding a tumor. Thus, in certain instances sites administration of attenuated Mycobacterial composition may be near the axillary, inguinal, anterior cervical, posterior cervical, tonsillar, submandibular, sub mental or superclavicular lymph nodes. Such sites of administration may be on the right side, on the left side, or on both sides of the body. In certain very specific embodiments, attenuated Mycobacterial compositions are delivered to axillary, cervical and/or inguinal lymph nodes. For example, a dosage of the attenuated bacteria may distributed into tissues adjacent to the right and left axillary lymph node and the right and left inguinal lymph nodes. In a very specific embodiment a dosage of attenuated Mycobacteria is administered to a subject by intradermal injection wherein the dosage is distributed to the axillary and inguinal on both sides of the body and wherein there are two injections (i.e. two wheals) at each site.

In some further embodiments of the invention, methods of the invention involve the administration of 2, 3, 4, 5, 6, 7, 8, 9, 10 or more doses of attenuated Mycobacteria separated by a period of one day or more. In certain preferred embodiments such separate doses will be separated by several days, one week, two weeks, one month or more. Such a separation of the doses is preferable due to superficial abscess formation that typically accompanies such therapy. For example, methods according to the invention may comprise administering 1 to 5 doses of attenuated Mycobacteria over a period of three weeks or more. In yet further embodiments, methods of the invention comprise administering 1 to 5, 1 to 4, 1 to 3, 1 to 2 or 2 doses of attenuated Mycobacteria over a period of about three weeks. Each dose administered may be the same or different dosage relative to a previous or subsequent dose administration. For example, in certain cases, it is preferred that a dosage of attenuated Mycobacteria is lower than any dosage that was previously administered. Thus, in some specific cases, a dose of attenuated Mycobacteria will be administered at about half of the dosage that was administered in any previous treatment. Such methods are preferred in certain instances since the a subject's immune response to the Mycobacteria is expected to be greater during subsequent therapies. Thus in certain cases, it may be preferred that an attenuated Mycobacterial immunotherapy be administered a minimal number of times for example, in less than 10, 9, 8, 7, 6, 5, 4, 3 or fewer separate dosage administrations. In some cases the attenuated Mycobacterial composition is administered twice.

In yet further embodiments, methods of the invention involve determining whether a subject has an immune response to a *Mycobacterium*. The most common method for determining whether a subject has an immune response to Mycobacteria by a standard skin test using the Mycobacterial antigen termed the purified protein derivative (PPD). The test involves introducing PPD into the skin, typically on the forearm of a subject, and measuring the diameter of any induration 48 to 72 hours after administration of the antigen. In general, subjects with indurations less than 10 mm in diameter are considered negative for a Mycobacterial immune response. On the other hand, induration of 10 mm or more indicates that a subject is positive for a Mycobacterial immune response. This type of PPD skin test is also semi quantitative in that a larger diameter induration is indicative of a greater immune response to Mycobacteria. Thus, in certain embodiments of the invention, a subject is tested to determine whether said subject has an immune response to Mycobacteria prior to the administration of attenuated Mycobacterial compositions according to the invention. In some very specific cases, testing a subject for an immune response to Mycobacteria will comprise administering a PPD skin test and measuring the diameter of any induration 48 to 72 hours after administration.

In yet further embodiments of the present invention, the dosage of attenuated Mycobacteria administered to a subject is modified depending on whether the subject has a Mycobacterial immune response. For example, in certain cases subjects that test positive in a PPD skin test are administered a lower dosage of attenuated Mycobacteria. Conversely, subjects that test negative in a PPD skin test may be administered a higher dosage of attenuated Mycobacteria. As discussed above, since PPD skin tests are semi quantitative, the dosage of attenuated Mycobacteria administered to a subject is, in some cases, inversely proportional to the diameter of the induration observed in the skin test. In some very specific examples, the dosage of attenuated Mycobacteria administered to a subject with a 10-20 mm PPD induration is about half the dosage that is administered to a subject who has less than a 10 mm PPD induration. Furthermore, a subject with an induration greater than 20 mm in diameter may be administered a dosage of attenuated Mycobacteria that is about one quarter of the dosage administered to a subject with a negative in a PPD skin test (i.e. a subject with an induration that is less than 10 mm in diameter). For instance, if a PPD negative subject is administered at about $3 \times 10^6$ CFU of attenuated Mycobacteria, then a subject with a 10-20 mm induration is administered about $1.5 \times 10^6$ CFU and a subject with a greater than 20 mm PPD induration is administered about $7.5 \times 10^5$ CFU of attenuated Mycobacteria. Thus, it will be understood that in certain embodiments the instant invention provides a method for preventing or treating a tumor in a subject comprising administering to the subject a PPD skin test and then administering to said subject a therapeutically effective dosage of an attenuated Mycobacterial composition according to the invention wherein the dosage of attenuated Mycobacteria is adjusted based upon whether said subject has an immune response to Mycobacteria.

In some further embodiments, methods according to the invention additionally involve a second therapy of a cancer or malignant tumor. For example, in certain cases attenuated Mycobacteria according to the invention will be used in combination or in conjunction with chemotherapy, radiotherapy, gene therapy, immunotherapy and/or surgical therapy. Such additional therapies can be administered before, after or essentially concomitantly with an attenuated Mycobacterial compositions. In certain cases chemo therapy agents such as paclitaxel, gemcitabin, 5-fluorouracil, etoposide, cisplatin, capothecin, vincristine, VELCADE®, doxorubicin, dacarbazine or a combination or derivative thereof may be used along with the methods described herein. In addition, it may be preferable to employ a surgical therapy in conjunction with the Mycobacterial immunotherapy of the invention. For example, surgical resection or partial resection of primary or metastatic tumors is a highly preferred additional therapy. In these cases, the immunotherapeutic Mycobacterial compositions of the invention may be used as a post surgical adjuvant to prevent the recurrence of cancer and/or prolong survival of a subject. Thus, in some specific cases, methods of the invention comprise surgical resection or partial resection of one or more malignant tumors followed by administration of an attenuated Mycobacterial composition according to the invention.

Methods according to the invention can be used to treat a variety of malignant tumors. For example in some embodiments, methods according to the invention are used to treat a subject with a lung, breast, brain, prostate, spleen, pancreatic, cervical, ovarian, head and neck, esophageal, liver, skin, kidney, gastric, bone, testicular, colon or bladder cancer tumor. For example, methods of the invention may be used to treat subjects with melanoma, such as a stage I, stage II, stage III or stage IV melanoma. In yet a more preferred embodiments, methods of the invention are used to treat a subject with a malignant tumor that is positive for one or more tumor specific antigens. As used herein the term tumor "specific antigen" refers to an antigen such as a protein, glycoprotein or carbohydrate that is expressed specifically or preferentially on cancer cells. For example, in certain embodiments, methods according to the invention may be used to treat a subject with a tumor comprising a urinary tumor specific antigen such as a UTAA (e.g., TA90) antigen positive tumor.

A particular advantage of the methods of the present invention is that attenuated Mycobacterial compositions can be used to induce an immune response against a tumor specific antigen. For example methods according to the invention may induce a humoral and/or a cell-mediated immune response to cancer or tumor specific antigens thereby directing the subject's immune system to destroy cancer cells in the subject. Such immune response may involve, for example antibodies, B-cells, CD4$^+$ T-cells and CD8$^+$ T-cells (i.e. cytotoxic). Both antibody and cell mediated immune responses can be induced by methods of the invention. Thus, in certain embodiments, there is provided a method for preventing or treating a tumor or cancer in a subject comprising administering to the subject a therapeutically effective dosage of an attenuated Mycobacterial composition of the invention wherein said attenuated Mycobacterial composition induces an immune response directed against a cancer or tumor specific antigen.

In certain embodiments of the invention, a subject's response to an immunotherapy may be monitored. For example, immune response to a tumor or cancer specific antigen can be monitored. By monitoring the subjects immune response to such an antigen following Mycobacteria administration the effectiveness of the therapy can be determined. Thus, in certain cases wherein low or negligible stimulation of a cancer specific immune response is detected following an administration of an attenuated Mycobacterial composition, therapy may be modified. For example, other therapeutic regimens such as chemotherapy, surgical therapy, radiation therapy or gene therapy may be administered. In certain case wherein a low or negligible tumor specific immune response is detected an additional dose of attenuated Mycobacteria may be administered to the subject. Such an additional dose may be a lower or higher dosage relative to the previous administration. However, in certain instances it may be preferable to increase the dosage of attenuated Mycobacteria in order to further stimulate the subject's immune system. It will be understood by one of skill in the art that in order to accurately determine whether Mycobacterial immunotherapy is stimulating a cancer specific immune response, the subject's immune response will in some cases be tested before and after administration of attenuated Mycobacteria. In certain cases, it is preferable to determine a subject's immune response to an immunotherapy soon after the initial administration of the therapy. For example, in certain cases a cancer specific immune response may be determined 6, 5, 4 or three months or less after the initial administration of a Mycobacterial immunotherapy. Thus, in certain embodiments the invention provides a method for determining whether a subject is responding to a Mycobacterial immunotherapy comprising measuring the subjects immune response to a cancer specific antigen before and after administration of an attenuated Mycobacterial composition of the invention.

A variety of methods can be employed in order to determine or measure a subject's immune response to a tumor or cancer specific antigen. For example in some embodiments an immune response may be determined by detecting antibodies specific for a particular cancer or cancer antigen. Thus, in some cases the concentration or titer of such antibodies is indicative of the level or strength of the immune response to a particular antigen. It will be understood by one of skill in the art that detection of antibodies to a particular antigen can also indicate the strength of an immune response in general (i.e. both a humoral and cell mediated immune response). For example, cancer specific antibodies in a subject can be measured by enzyme-linked immunosorbent assay (ELISA), immunofluorescence or immunoblot. Such methods may also be used to determine the types of tumor specific antibodies in a individual. In some very specific embodiments a cancer specific immune response may be detected or measured by detecting urinary tumor associated antigen (UTAA) specific antibodies such as TA90 specific antibodies in a subject. An exemplary method for such detection is described in U.S. Pat. Nos. 5,700,649 and 5,993,828 incorporated herein by reference. For example, the titers of cancer specific IgA, IgB, IgG, IgM or IgE may be determined. Other methods can also be used to measure a subject's immune response to cancer specific antigens, for example levels of specific cytotoxic T-cells can be determined directly by chromium release assays or by directly observing cell infiltration into malignant tumors (i.e. by immunohistochemical analysis). In some very specific cases, the invention provides a method for determining whether a subject with a malignant tumor is responding to a Mycobacterial immunotherapy comprising measuring the titer of tumor specific antibodies in the subject before and after administration of an attenuated Mycobacterial composition according to the invention.

In certain embodiments of the invention, it is preferable that a particular dosage of attenuated *Mycobacterium* be administered to a subject. Thus, in certain embodiments of the invention, there is provided a containment means comprising 1 to 5 unit doses of attenuated Mycobacteria wherein each unit dose comprises about $1 \times 10^4$ to about $1 \times 10^7$ CFU of attenuated Mycobacteria. In some further embodiments of the invention, there is provided a composition comprising 1 to 5 unit doses of about $1 \times 10^5$ to about $5 \times 10^6$ CFU of attenuated Mycobacteria in a suitable containment means. In very specific embodiments of the invention, there is also provided a composition comprising; 1 unit dose of about $3 \times 10^6$ attenuated Mycobacteria, 2 unit doses of about $1.5 \times 10^6$ attenuated Mycobacteria, or 4 unit doses of about $7.5 \times 10^5$ attenuated Mycobacteria in a suitable containment means. A container according to the invention in certain instances, may be a vial, an ampoule, a syringe or a tube. In some cases, the attenuated Mycobacteria may be lyophilized and formulated for resuspension prior to administration. However, in other cases, the attenuated Mycobacteria are suspended in a volume of a pharmaceutically acceptable liquid. In some of the most preferred embodiments there is provided a container comprising a single unit dose of attenuated Mycobacteria suspended in pharmaceutically acceptable carrier wherein the unit dose comprises about $1 \times 10^5$ to about $1 \times 10^7$ CFU of attenuated Mycobacteria. In some very specific embodiments the liquid comprising suspended Mycobacteria is provided in a volume of between about 0.1 ml and 10 mls, or about 0.5 ml and 2 mls. In very specific case the suspended Mycobacteria are provided in a volume of about 1 ml. It will further be understood that in certain instances a composition comprising Mycobacteria in a containment means is frozen (i.e. maintained at less than about 0° C.). The foregoing compositions provide ideal units for immunotherapeutic applications described herein.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawing is part of the present specification and is included to further demonstrate certain aspects of the present invention. The invention may be better understood by reference to the drawing in combination with the detailed description of specific embodiments presented herein.

FIG. 3a, 5 year survival rates for patients with stage III melanoma and indicated numbers of positive nodes from databases and multicenter adjuvant trials versus MCV+BCG or BCG+placebo. FIG. 3b, 5 year survival rates for patients with stage III melanoma from databases and multicenter adjuvant trials vs MCV+BCG or BCG+placebo. A sixth trial, Gimotty (SEER), resulted in a 53.7% five year survival rate.

FIG. 5: Kaplan-Meier Estimates of the over-all five year survival for Stage IV melanoma patients that had soft tissue and nodal metastases when treated with MCV+BCG or BCG+placebo. Results are represented numerically on the upper right.

FIG. 6: Stage IV melanoma patients treated with melanoma cell vaccine+BCG exhibited superior five year survival rates as compared to patients treated in other clinical trials (from a database). However, therapy with BCG alone was significantly more effective than MCV+BCG therapy. FIG. 6, shows a comparison of median survival (in months) and five years survival rates in patients with stage IV M1a following complete resection. Results from the indicated studies are compared to results from BCG treated patients.

DETAILED DESCRIPTION OF THE INVENTION

The clinical trial described herein was initially designed to test the efficacy of melanoma cell vaccine (e.g., CAN-VAXIN™), an anti-cancer vaccine previously described in U.S. Pat. Nos. 6,168,787 and 5,882,654. At the time of the trials inception it was generally considered that co administration of BCG may enhance immune response to the MCV resulting in a more robust immune response to the cancer. However, except when directly applied to tumor tissue, BCG administration alone has failed to demonstrate anticancer efficacy when tested in clinical trials. Thus, the BCG therapy alone was used as the negative control for the present studies in which the MCV was tested in Stage III and IV melanoma patients. However, contrary to previous studies, Mycobacteria administered the protocol in this new trial did prove to be an effective cancer therapy.

Figure 3A:
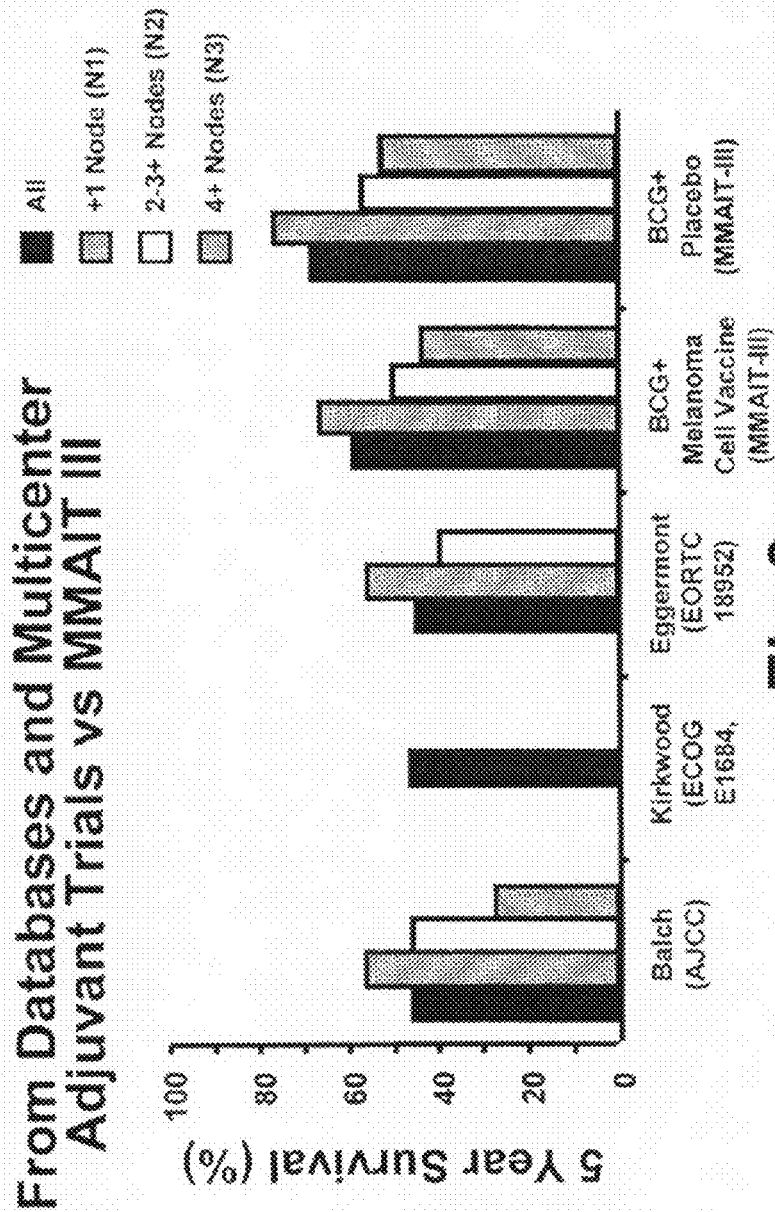
FIG. 3a-b: Stage III melanoma patients treated with melanoma cell vaccine+BCG exhibited superior five year survival rates as compared to patients treated in other clinical trials (from a database). However, therapy with BCG alone was significantly more effective than MCV+BCG therapy.
Figure 3B:
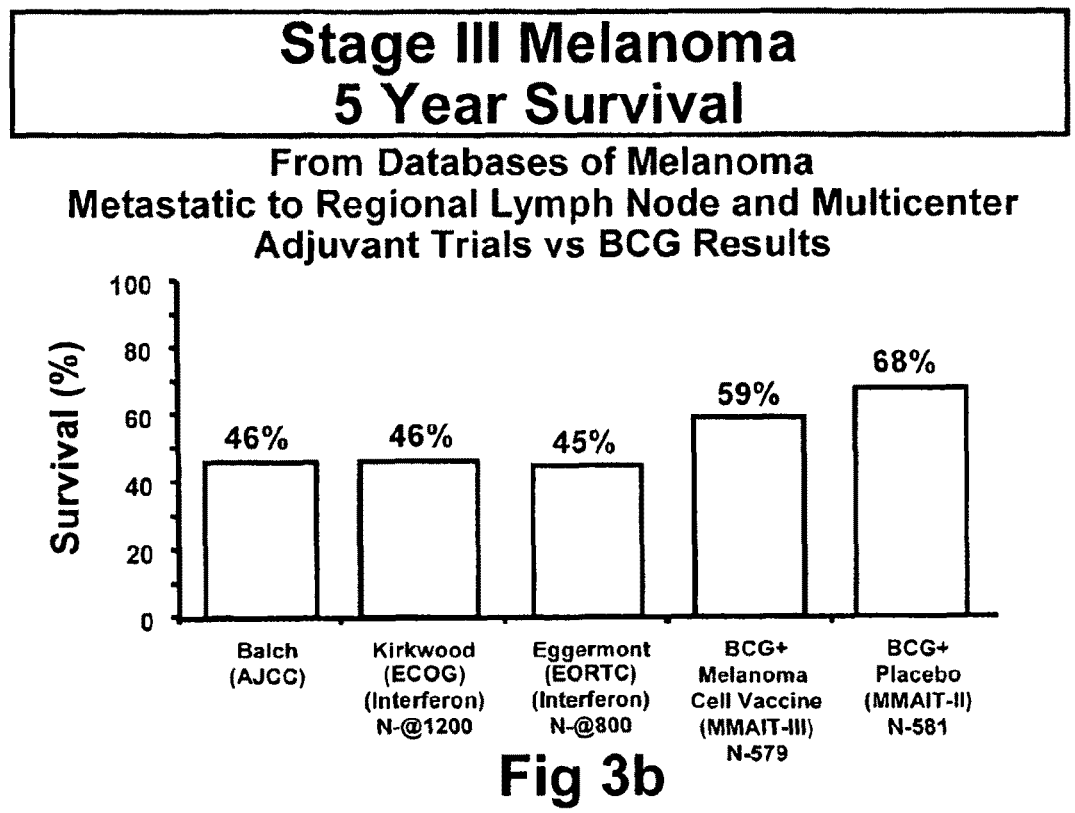
Figure 4:
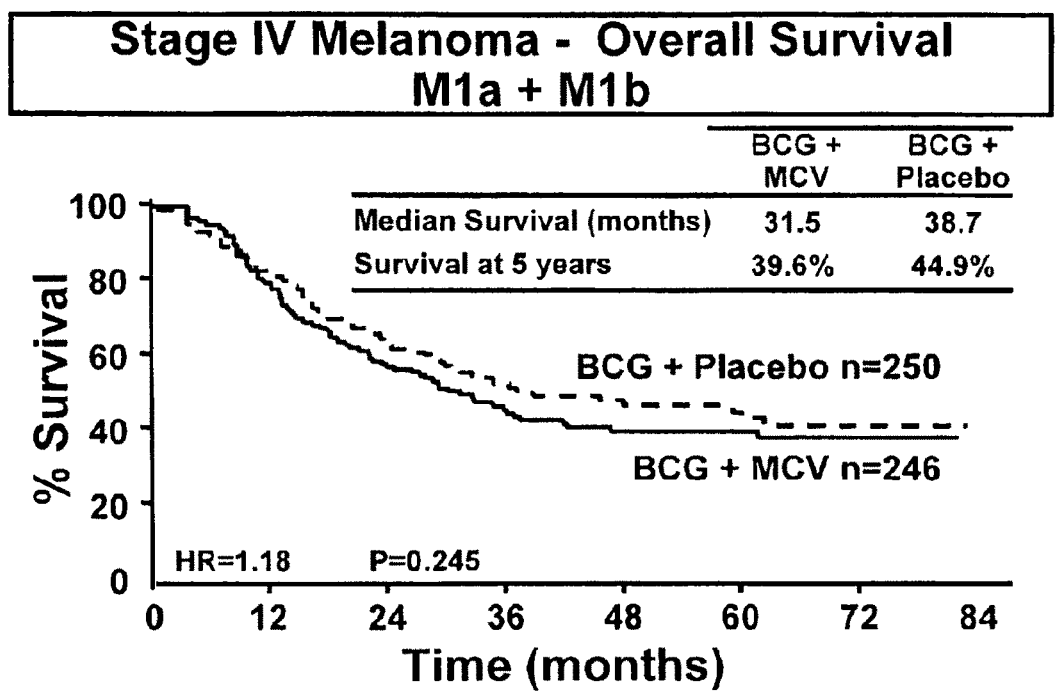
FIG. 4: Kaplan-Meier Estimates of the over-all five year survival for Stage IV melanoma patients treated with MCV+BCG or BCG+placebo. Results are represented numerically on the upper right.

As the results of the present trial accumulated is became clear that BCG therapy alone was in fact more effective in treatment and prevention cancer than BCG in addition to MCV. Furthermore, as shown in FIG. 3b, the BCG therapy was more effective at preventing recurrence of cancer than many other experimental therapeutic regimens. Thus, the novel BCG administration protocols described herein rendered the Mycobacterial therapy effective, in contrast to the prior art therapies that failed to show such efficacy. Yet more interesting, was the observation the Mycobacteria administration actually resulted in a tumor specific immune response, despite the fact that BCG was administered in the absence of MCV.

Further analysis of the data described herein revealed yet another useful aspect of the new Mycobacterial therapy. It is now shown that the tumor specific immune response elicited by the Mycobacteria can be used as diagnostic factor to predict the efficacy of the therapy. In particular, it is shown that UTAA IgG titer (e.g., anti-TA90 IgG titer) in Mycobacteria treated patients is an excellent predictor of clinical outcome. In fact, antigen specific IgG titers that are measured a little as three months after the initial administration of the Mycobacteria are predictive of the long term prognosis of treated subjects.

Based on these new discoveries the instant invention provides a novel and effective treatment for cancer by administration of attenuated Mycobacterial compositions. These compositions are essentially free of melanoma cells and administered to non-tumor tissues or sites in the body do not coincide with a tumor. These methods can, in some preferred embodiments, be used as post-surgical adjuvants to prevent the recurrence of disease. The attenuated Mycobacterial composes are shown to mediate a cancer specific immune response in treated subjects. Thus, immune responses induced by the immunotherapies of the invention may be used to monitor and/or predict the effectiveness of the therapy. In cases in which there is little immune response to Mycobacterial therapy other treatment avenues and/or additional doses of attenuated Mycobacteria may be administered thereby enabling much more effective treatments for cancers The invention also provides composition for use in such immunotherapeutic regimens. In certain embodiments of the invention, attenuated Mycobacteria are delivered by intradermal injection of less that about 10 million colony forming units. Thus in certain embodiments there is provided a composition comprising 1 to 5 dose units wherein each dose unit comprises about $1 \times 10^4$ to about $1 \times 10^7$ CFU of attenuated Mycobacteria packaged in a suitable containment means. Compositions such are ideal for therapy and in some case would be proved in single dose unit aliquots providing quick and convenient therapeutic tools. More specific embodiments of methods and compositions of the invention are described below.

I. Mycobacterial Immunotherapeutic compositions

Attenuated Mycobacterial compositions for use in the current invention will be essentially free of melanoma cells. However, in certain cases, they comprise tumor antigens that are not associated with melanoma cells. For example, in some cases the Mycobacteria itself may express one or more tumor antigens (e.g., a Mycobacteria may be transformed with an expression cassette comprising one or more tumor antigens).

Attenuated Mycobacteria for use in the instant invention may comprise a variety of different Mycobacterial species strains or sub-strains, and may in come cases comprise a mixture thereof. For example, attenuated Mycobacteria may be derived from *Mycobacterium africanum, Mycobacterium canetti, Mycobacterium microti* or *Mycobacterium bovis*. In some specific cases the Mycobacteria may be attenuated BCG bacteria such as the Pasteur, Tice® or RIVM sub-strains of BCG. It will be understood that in some instances the Mycobacteria of the invention is provided as live bacteria that is capable of proliferation, however the bacteria may in some cases be "killed," for instance by heat inactivation.

Attenuated Mycobacterial compositions will comprise an effective amount of Mycobacterial typically dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains Mycobacteria will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards. A specific example of a pharmacologically acceptable carrier as described herein is the sterile saline solution (0.9% NaCl) with or without placebo (RPMI 1640 with 8% human serum albumin and 20% (by volume) RIMSO®-50).

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

Though in highly preferred embodiments of the invention attenuated Mycobacterial compositions are administered by direct intradermal injection, it is also contemplated that other methods of administration may be used in some cases. However, it will be understood by one of skill in the art that any form of systemic administration will preferably involve a low dosage Mycobacterial composition. For example, a low dosage composition may comprise less than about $1\times10^7$, $1\times10^6$ or $1\times10^5$ to about $1\times10^4$ CFU of attenuated Mycobacteria. Thus in certain instances attenuated Mycobacteria of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as PPD antigen reactivity, general immune status, body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 5 mg/kg/body weight to about 100 mg/kg/body weight, about 5 microgram/kg/body weight to about 500 milligram/kg/body weight, etc., can be administered, based on the numbers described above.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

In particular embodiments, prolonged absorption of an injectable composition can be brought about by the use in the compositions of agents delaying absorption, such as, for example, aluminum monostearate, gelatin or combinations thereof.

II. Diseases for Treatment with Immunotherapeutic Compositions of the Invention

As described above, methods of the invention involve administration of attenuated Mycobacterial compositions for the treatment of cancer, such as malignant tumors. Cancers that may be treated according to the invention include but are not limited to cells or neoplasms from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

III. Additional Anticancer Therapies

As outline above in certain cases, immunotherapy according to the invention will also comprise additional anticancer therapies administered before, after or essentially concomitantly with attenuated Mycobacterial compositions. Some examples of such additional therapies are outlined below, though methods of the invention are in no way limited to the additional therapies listed.

Chemotherapy

In certain embodiments of the invention attenuated *Mycobacterium* compositions according to the invention are administered in conjunction of combination with a chemo therapeutic agent. For example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, gemcitabien, navelbine, farnesyl-protein tansferase inhibitors, transplatinum, 5-fluorouracil, vincristin, Velcade, vinblastin and methotrexate, or any analog or derivative variant of the foregoing may used in methods according to the invention.

Radiotherapy

In certain embodiments methods of the invention may be used in combination with radiation therapy. Radio therapy may include, for example, γ-rays, X-rays, and/or the directed delivery of radioisotopes to tumor cells. In certain instances microwaves and/or UV-irradiation may also used according to methods of the invention. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radio therapeutic agent are delivered to a target cell or are placed in direct juxtaposition with the target cell. To achieve cell killing or stasis, both agents are delivered to a cell in a combined amount effective to kill the cell or prevent it from dividing.

Additional Immunotherapies

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B, Her-2/neu, gp240 and p155.

Gene Therapy

In yet another embodiment, gene therapy in which a therapeutic polynucleotide is administered before, after, or at the same time as a cell targeting construct of the present invention. A variety of genes are encompassed within the invention, for example a gene encoding p53 may be delivered in conjunction attenuated Mycobacterial compositions.

Surgery

Approximately 60% of persons with cancer will undergo surgery of some type, which includes preventative, diagnostic or staging, curative and palliative surgery. Curative surgery is a cancer treatment that may be used alone or in conjunction with other therapies, such as the treatment of the present invention, chemotherapy, radiotherapy, hormonal therapy, gene therapy, immunotherapy and/or alternative therapies. Attenuated Mycobacterial compositions of the present invention may be employed alone or in combination with a cytotoxic therapy as neoadjuvant surgical therapy, such as to reduce tumor size prior to resection, or it may be employed as postadjuvant surgical therapy, such as to sterilize a surgical bed following removal of part or all of a tumor.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Other Agents Anticancer Agents

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

IV. Detecting or Measuring Immune Responses

In still further embodiments, the present invention concerns immunodetection methods for binding, purifying, removing, quantifying and/or otherwise generally detecting biological components that are indicative of immune cell activation. In particular such methods are used to detect a cancer cell specific immune response. Such a response may be for example a cytotoxic T-cell response, an inflammatory T-cell response or a an antibody response (i.e., a response directed against a UTAA such as the TA90 antigen). Such methods may in some cases be used to determine or predict the efficacy of Mycobacterial immunotherapy. Some immunodetection methods include enzyme linked immunosorbent assay (ELISA), radioimmunoassay (RIA), immunoradiometric assay, fluoroimmunoassay, chemiluminescent assay, bioluminescent assay, Western blot, fluorescence activated cell sorting (FACS), and chromium release assay to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

These methods include methods for purifying an indicator of immune activation such as an antibody from a cell, tissue or other sample from a subject. In certain cases this may be accomplished by using an antibody or antigen specific for the particular immune activation indicator. The antibody or antigen will preferably be linked to a solid support, such as in the form of a column matrix, and the sample will be applied to the immobilized antibody. The unwanted components will be washed from the column or support, leaving the immunocomplex.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149; 4,366,241; and particularly U.S. Pat. Nos. 5,700,649, and 5,993,828, each incorporated herein by reference. Of course, one may find additional advantages through the use of a secondary binding ligand such as a second antibody and/or a biotin/avidin ligand binding arrangement, as is known in the art.

An antibody or antigen employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

ELISA

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, an immune cell activation marker such as a TA90 specific antibody is immobilized onto a selected surface exhibiting protein affinity, such as a well in a polystyrene microliter plate that has been coated with a specific antigen (i.e. TA90). After binding and/or washing to remove non-specifically bound immune complexes, the bound antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing an indicator of immune cell activation is immobilized onto the well surface and/or then contacted with an antibody. After binding and/or washing to remove non-specifically bound immune complexes, the bound antibodies are detected. Where the antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an indicator of immune cell activation in an unknown sample is then determined by mixing the sample with the labeled antibodies against the antigen during incubation with coated wells. The presence of the indicator in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface. For example is some specific embodiments an ELISA plate is coated with TA90 antigen for subsequent detection of TA90 specific antibodies.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

Immunohistochemistry

Methods of preparing tissue blocks from these particulate specimens has been successfully used in previous IHC studies of various prognostic factors, and/or is well known to those of skill in the art (Brown et al., 1990; Abbondanzo et al., 1990; Allred et al., 1990). In this case such methods may be used for example to detect caner specifci antibodies of immune cells in a biopsy sample.

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Clinical Trial Design and Protocols

The initial objective of the clinical trials was to determine whether adjuvant MCV plus BCG or BCG plus placebo will effectively prolong overall and disease-free survival in Stage III or Stage IV melanoma patients rendered NED (no evidence of disease) after surgical resection.

Trial Design:

The trial was a Phase III, randomized, multicenter, trial of immunotherapy with MCV plus BCG versus BCG alone as a post-surgical treatment for patients with Stage III or IV melanoma. Patients with Stage IV melanoma had visceral metastases or soft tissue and nodal metastases prior to surgical therapy. All patients were randomized to receive either MCV plus BCG or BCG plus placebo over a period of three years. Only the first two doses of each agent was administered with BCG. Patients were accrued at a number of national and international sites.

Treatments:

BCG: Care should be taken by those personnel handling BCG to avoid contact with the product as contact with BCG may cause conversion to tuberculin reactivity. Tice® Strain BCG (Organon Technica) was used as the source of the BCG in each case. Because individual lots vary in the number of viable organisms, a specific lot of known viability has been selected. Detailed instructions on how to obtain the correct dosage are included with each lot. The vials of lyophilized BCG were reconstituted according to the manufacturer's instructions. Reconstituted material may be stored at 2-8° C. for six hours.

Dosing was based on the subject's PPD status with tuberculin-negative subjects receiving $3 \times 10^6$ CFU added to MCV or placebo on day 0 and $1.5 \times 10^6$ CFU on day 14. Dose was reduced 50% for tuberculin-positive patients (i.e. with PPD indurations of 10 mm but less than 20 mm) and reduced by 75% (25% of PPD negative dosage) in subjects with a strong PPD response (i.e. indurations of 20 mm or greater), see Table 1. In each case, BCG was administered by intradermal injection as indicated during initial immunization and during reinduction on days 0 and 14.

TABLE 1

BCG Doses Administered as Determined based on PPD test results

| Skin test response to 5 test units of the intermediate strength PPD (diameter of induration) | First BCG inoculation dose | Second BCG inoculation dose |
|---|---|---|
| Negative < 10 mm | $3 \times 10^6$ CFU* | $1.5 \times 10^6$ CFU* |
| Positive ≥ 10 mm | $1.5 \times 10^6$ CFU* | $.75 \times 10^6$ CFU* |
| Positive ≥ 20 mm or past history of active tuberculosis | $.75 \times 10^6$ CFU* | $.37 \times 10^6$ CFU* |

*CFU—Colony Forming Units

Preparation of BCG Stock Solution for Initial Induction

All BCG used in this study will be Tice® strain (*Mycobacterium bovis*) manufactured by Organon Technica Corporation (Durham, N.C.). All BCG used will be from lot #451A011, which has been assayed at $1.8 \times 10^8$ CFU per ampoule of lyophilized preparation. This preparation will be stored at 2-8° C. until used.

At the time of use, a vial will be removed from cold storage 2-8° C. and the sealed glass ampoule opened. The contents will be diluted with 15 cc of sterile normal saline (0.9% sodium chloride) without preservative. This preparation will be replaced into the sterile saline vial that has been emptied of excess saline after cleansing the rubber stopper with isopropyl alcohol. The suspension will then be agitated to assure even suspension. This maneuver will be repeated before withdrawing each dose of product for use. The vial (Solution A) will be appropriately labeled as containing $1.2 \times 10^6$ CFU per 0.1 cc. An initial dosage of 3.0 million CFU would require 0.25 cc of Solution A. The second treatment will require 1.5 million CFU or 0.13 cc of Solution A. Modifications of dosage for tuberculin-positive patients are made in keeping with Table 1.

Using a tuberculin-type syringe (fused needle recommended) the needed volume of Solution A is removed from the vial and reserved for addition to the MCV or placebo preparation. The appropriate aliquot of BCG will then be added to this preparation just before administration. The mixture will be agitated at the time of addition of the BCG for 15 seconds and again immediately prior to administration for 15 seconds to assure even suspension of both vaccine cells and BCG. Administration of BCG plus placebo or plus MCV is detailed below.

Placebo: Was from a single-dose cryovial in each case. Each dose contained 0.5 ml of RPMI 1640 containing 8% human serum albumin and 20% (by volume) RIMSO®-50. For administration, 0.5 ml of 0.9% NaCl USP (without preservative) is added, giving a total volume of 1.0 ml administered in combination with BCG.

The first two doses (Days 0 and 14) of MCV or placebo are admixed with BCG as an immune adjuvant. The second dose is admixed with one-half the amount of BCG required for the same patient. The dosages of BCG for any given patient are determined by the patient's tuberculin reactivity status (see Table 1).

Subjects who develop melanoma recurrences will undergo reinduction whereby, lower dose BCG is mixed with MCV or placebo during the reinduction phase of immunization designed to induce a secondary response to melanoma antigens. The number of BCG organisms used in the reinduction phase is $2.0 \times 10^4$ on day 0 and $1 \times 10^4$ on day 14. No BCG is administered thereafter except during reinduction for another recurrence.

Melanoma Cell Vaccine: A single-dose cryovial was used containing a dosage of $25 \times 10^6$ viable lethally irradiated melanoma cells suspended in 0.5 ml of RPMI 1640 with 8% human serum albumin and 20% (by volume) RIMSO®-50, a 1:1 mixture of dimethyl sulfoxide and water. For administration, 0.5 ml of 0.9% NaCl USP (without preservative) is added, giving a total volume of 1.0 ml. In each case the MCV was administration via intradermal injection on days 0, 14, 28, 42 and 56; then monthly through year one, every 2 months during year 2, and every 3 months in years 3-5. Following recurrence, reinduction schedule was on days 0, 14, 28 and 42; then monthly.

The first two doses of MCV are administered in conjunction with BCG, as an immune adjuvant admixed in an identical way with each vaccine dose. After determining the appropriate BCG dosage level by the patient's tuberculin reactivity status, the correct volume of BCG suspension is drawn up into a tuberculin syringe and reserved for addition to the vaccine just before administration. To add BCG to the MCV, the 18-gauge needle is removed from the 3-ml syringe containing the saline/MCV mixture and, using the tuberculin syringe, the requited amount of BCG is injected into the 3-ml syringe. A 26-gauge needle is affixed to the syringe, making it ready for administration. The syringe is gently inverted several times at this point and again immediately before administration to assure homogeneous suspension of the cells and the BCG.

At the time of administration, after gentle mixing, any bubbles in the syringe are carefully expressed with the syringe held in an inverted position. After cleaning the skin with an alcohol swab, the MCV suspension is injected intradermally to form an intradermal wheals of 0.125 to 0.128 ml at each of four sites (the right and left inguinal areas and the right and left axillary chest walls). The syringe and needle are then disposed of in an appropriate manner. The second MCV dosage is routinely administered with one-half of the BCG dosage level provided in the initial MCV inoculation using the same techniques.

Except for instances of reinduction, the third and all subsequence doses of MCV are admixed with Sterile Sodium Chloride for injection without preservative only. MCV must be administered immediately, within 20 minutes after thawing.

Preparation of BCG Solution for Reinduction

A further diluted working solution of BCG (Solution B) is prepared from the stock solution (Solution A). Solution B, containing 20,000 CFU per 0.1 cc, is prepared by drawing up 0.5 cc of Solution A and placing it in a small sterile ampoule with a rubber stopper. To this aliquot of Solution A, 29.5 cc of sterile normal saline (0.9% sodium chloride) is added and agitated to assure even suspension. This solution will provide material for reinduction dosages of 20,000 and 10,000 CFU in 0.1 and 0.05 cc. This ampoule should be marked with a distinctively colored label bearing the designation "Solution B containing 20,000 CFU per 0.1 cc for reinduction."

Appropriate volumes will be drawing from Solution B to correspond with the needed dosage of BCG for the treatment schedule using a tuberculin syringe (fused needle type recommended). The appropriate aliquot of BCG will then be added to the MCV or placebo preparation just before administration. The mixture will be agitated at the time of addition of the BCG for 15 seconds and again immediately prior to administration for 15 seconds to assure even suspension of both vaccine cells and BCG.

Additional Medications for Patient Comfort

In certain instance additional medications are given to subjects in reduce discomfort from immunotherapy.

Acetaminophen: Patients may receive up to 1,000 mg by mouth every 4 hours (maximum to 4,000 mg/day). It should be used as necessary as determined by the patient's subjective side effect.

Benadryl: Patients may receive up to 50 mg by mouth every 4 hours as needed to counteract the local redness, itching or general myalgias related to the treatment. It should be used as necessary as determined by the patient's subjective side effects.

Example 2

Evaluation of Clinical Trial Results

The primary endpoint for the trial was overall survival of subjects who were administered to the various treatment regimens. However, additional end point included (1) disease-free survival, (2) the clinical outcomes of immunological responders and non-responders, (3) TA-90 immune complex and multi-marker RT/PCR assays to identify patients at high risk for recurrence and (4) quality of life parameters. Safety is evaluated in the study by review of adverse events, clinical laboratory tests, vital signs, physical examinations and nursing assessments.

MCV Associated Side Effects

All systemic symptoms observed were mild to moderate in intensity and transient. Patients receiving MCV have experienced transient low-grade fever (27%), chills (24%), arthralgias (0.5%), myalgias (36%), headache (13%). The most frequent side effect is fatigue, which occurs n 74% of patients transiently for 24-36 hours following administration. Frequently occurring side effects included localized stinging, itching and redness where the placebo is injected. While side effects that occurred occasionally included generalized flu-like symptoms including muscle aches, joint aches, fever, chills, loss of appetite, and/or fatigue BCG Associated Side Effects Nearly all patients receiving MCV in combination with BCG experienced local erythema, induration and inflammation of the skin at the vaccine injection sites. When administered intradermally, the expected reaction is a small red papule that scales, form as a localized abscess, ulcerates and dries, leaving a small pink or bluish scar after 6-12 weeks. In most instances, the individual inoculation sites also under go transient ulceration and these circumscribed ulcerations (from 2-8 mm in diameter) normally resolved and re-epithelialize within six to eight weeks. No bacterial super infection of these transient ulcerations has been encountered. About 1% of MCV-treated patients experienced transient localized rashes radiation outward from their injection sites but limited mainly to the torso. These rashes have cleared completely within 5 to 30 days. These skin reactions are attributable to the BCG (adjuvant) component of the vaccine and thus, are expected to occur following the first two vaccinations when MCV or placebo is administered conjointly with BCG.

More severe ulcerations and granulomas may occur in patients who are tuberculin-negative on initial testing but have a history of tuberculosis or previous BCG treatment. For this reason, two pre-study tuberculin tests are recommended to avoid use of higher dose BCG in such patients.

Other observed side effects included mild fever, chills, lethargy and malaise are observed in about 30% of patients following the first two treatments with BCG. Approximately 20% of patients develop enlargement and tenderness of lymph nodes. Rashes, lymphadenitis or lymphangitis also occur in a small proportion of patients. Disseminated BCG infection, tuberculosis meningitis, anaphylaxis, Guillain-Barre syndrome, and aplastic anemia have been reported rarely in patients receiving BCG as prophylaxis against tuberculosis, usually in the presence of immunodeficiency states. Although none of these has been observed in over 1,000 patients receiving BCG here, they are potential rare complications. The Tice® strain of BCG is very sensitive to both isoniazid (INH) and rifampin, which are commonly used for treatment of tuberculosis.

Overall and Disease Free Survival

Figure 1:
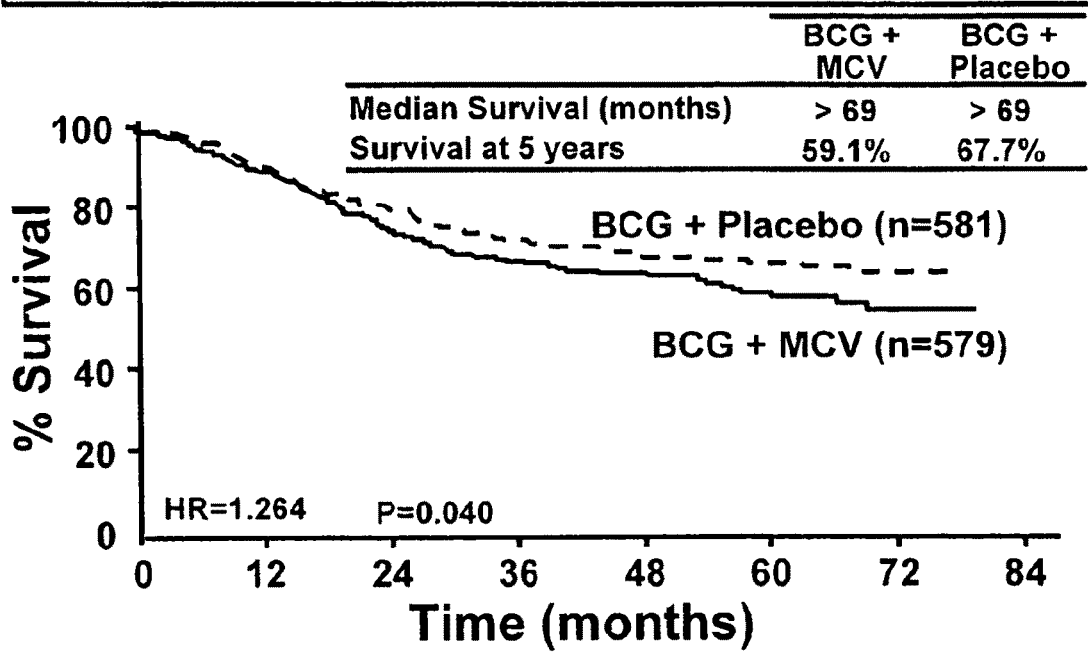
FIG. 1: Kaplan-Meier Estimates of the over-all five year survival for Stage III melanoma patients treated with Melanoma cell vaccine (MCV)+BCG or BCG+placebo. Results are represented numerically on the upper right.
Figure 2:
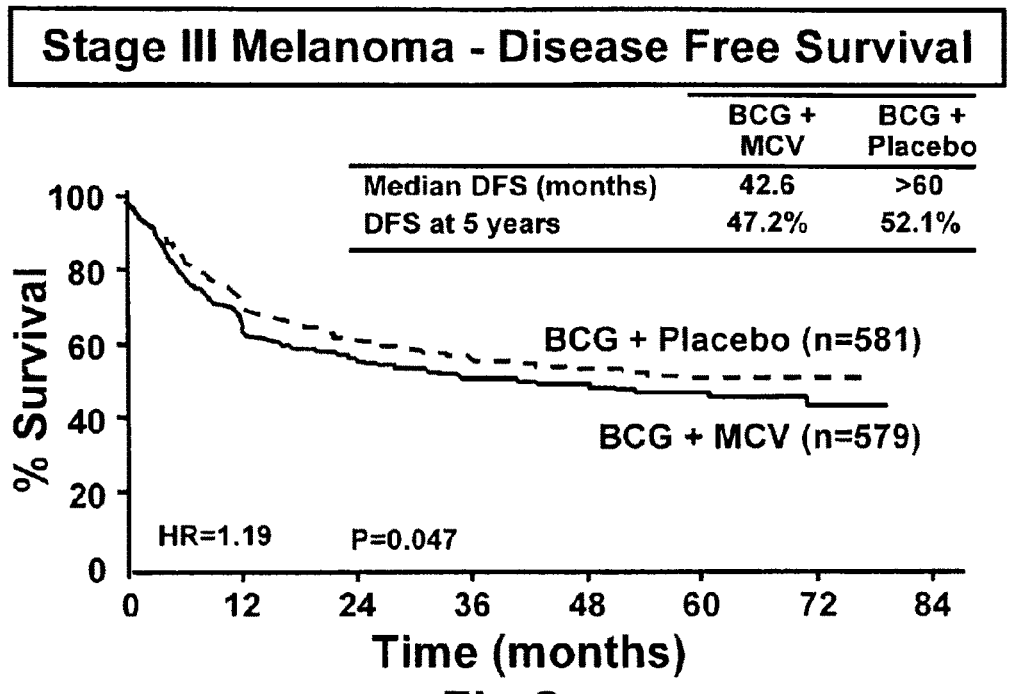
FIG. 2: Kaplan-Meier Estimates of the disease-free survival (DFS) over 5 years for Stage III melanoma patients treated with MCV+BCG or BCG+placebo. Results are represented numerically on the upper right.

FIG. 1-6 show the Kaplan-Meier Estimates for overall and disease free survival of trial patients over five years. In all cases, a greater proportion of subjects receiving BCG plus placebo are expected to survive the five year study period. The BCG only therapy is expected to provide enhanced survival in both stage III and stage IV melanoma patients as indicated in FIG. 1 and FIG. 2. This effect was maintained in subjects with visceral and nodal metastases as shown in FIG. 3a,b. Additionally, a greater proportion of the BCG only patients with Stage III melanoma are expected to enjoy disease free survival over the five period (FIG. 2). This a highly significant finding since as shown in FIG. 3b BCG therapy is more effective than previous regimens at increasing subject survival. Nonetheless, BCG therapy described herein is more effective than all other compared treatment regimens, including MCV BCG.

Example 3

UTAA Sero-Conversion

Following treatment of Stage III melanoma patients with either MCV plus BCG or BCG plus placebo blood was drawn periodically for the first 6 months to determine the TA90 specific IgG and IgM antibody titers. In each case, antibody titers were assessed by ELISA as described in Habal et al., 2001. Patients were categorized as responders or non-responders based on their TA90 IgM or IgG titers. For the purposes of analysis, subjects with TA 90 specific IgG titers of greater than 1:400 and TA90 specific IgM titers of greater that 1:800 were categorized as responders. In agreement with the results from over-all and disease free survival studies, a larger percentage of patients receiving BCG alone were categorized as responders based on IgG and IgM serum titers. At the three month time point ~50% of BCG alone patients had a greater then 1:400 TA90 IgG titer. By six months ~70% of the BCG group were responders (i.e. had IgG titer of greater then 400:1). These data indicate that BCG (plus placebo) administered in the absence of MCV was able to elicit a TA90 specific immune response.

Example 4

Antibody Titer is Predictive of BCG Therapeutic Efficacy

Following BCG administration to stage III melanoma patients total UTAA (TA90) specific IgG titer was determined at 3-months and at 6-months. Antibody titers were determined in each case by ELISA as previously described in Habal et al., 2001. These data were used to analyze the results of clinical trial by determining whether there is a correlation between TA90 specific IgG titer and positive response to the therapy (i.e. survival through a five year period). For the analysis trial subjects with a beginning (preadministration) TA90 IgG titer of ≥400 were not considered. The results of these analyses are shown in Tables 2 and 3.

TABLE 2

3-Month UTAA (TA90) IgG Titer Median and 5-year Survival

| Treatment | 3-Month TA90 IgG | n | Median | 5-year Survival * |
|---|---|---|---|---|
| BCG | <400 | 127 | >74.8 | 58.6% |
| BCG | ≥400 | 94 | >77.6 | 74.6% |

* = A statistically significant difference with a P value of 0.0908.

TABLE 3

6-Month UTAA (TA90) IgG Titer Median and 5-Year Survival

| Treatment | 3-Month TA90 IgG | n | Median | 5-year Survival * |
|---|---|---|---|---|
| BCG | <400 | 101 | >74.1 | 54.8% |
| BCG | ≥400 | 124 | >77.6 | 74.1% |

* = A statistically significant difference with a P value of 0.0218.

The foregoing studies indicate that the clinical prognosis of BCG treated subjects is correlated with TA90 specific IgG titer at both three and six months after the initial BCG administration. Specifically, subjects demonstrating a UTAA (TA90) IgG titer of greater than 400 were significantly more likely to positively response to the therapy and survive past the five year end point of the study. Thus, measuring BCG induced tumor response can be used to predict the clinical outcome of patients undergoing such therapy. The ability to predict the effectiveness of a BCG therapy as little as 3-months from the initial administration will enable additional therapies to implemented in the case where tumor specific immune response in weak. Thus, allowing for yet further improvements in the clinical outcome on cancer patients.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 5,882,654
U.S. Pat. No. 5,700,649
U.S. Pat. No. 5,840,317
U.S. Pat. No. 5,993,828
U.S. Pat. No. 6,168,787
Abbondanzo et al., *Breast Cancer Res. Treat.*, 16:182(151), 1990.
Agarwala et al., *Cancer*, 100(8):1692-1698, 2004.
Allred et al., *Breast Cancer Res. Treat.*, 16:182(149), 1990.
Brown et al. *Immunol. Ser.*, 53:69-82, 1990.
Czarnetzki et al., *Eur. J. Cancer*, 29A(9):1237-1242, 1993.
De Jager et al., *Semin. Nucl. Med.*, 23(2):165-179, 1993.
Doolittle and Ben-Zeev, *Methods Mol Biol*, 109:215-237, 1999.
Grange et al., *Tubercle* 64:129-139, 1983.
Gulbis and Galand, *Hum. Pathol.*, 24(12):1271-1285, 1993.
Habal et al., *Ann. Surg. Oncol.*, 8(5):389-401, 2001.
Lamm et al., *Urol Oncol*, 1:119-126, 1995.
Morton et al., *Med. Clin. North Am.*, 60(3):431-439, 1976.
Morton et al., *Surgery* 68:158-164, 1970.

Nakamura et al., In: *Handbook of Experimental Immunology* (4$^{th}$ Ed.), Weir et al. (Eds.), 1:27, Blackwell Scientific Publ., Oxford, 1987.

Pardridge et al., *Surg. Gynecol. Obstet.*, 148:867-870, 1979.

Remington's Pharmaceutical Sciences, 18th Ed. Mack Printing Company, 1990.

Silver et. al., *Can Med Assoc J*, 128:1291-1295, 1983.

Veronesi et al., *N. Engl. J. Med.*, 307(15):913-916, 1982.

Witjes et al., *Eur J Cancer*, 29A(12):1672-1676, 1993.

The invention claimed is:

1. A method for treating a malignant melanoma tumor in a subject comprising administering to the subject a therapeutically effective dosage of a bacille Calmette-Guerin (BCG) strain of attenuated Mycobacteria composition comprising $1\times10^4$ to $5\times10^7$ colony forming units (CFU) of Mycobacteria wherein said BCG composition is not administered directly to the tumor and wherein said composition is free of melanoma cells.

2. The method of claim 1, wherein said BCG composition is administered by direct intradermal injection into non-tumor tissue.

3. The method of claim 2, wherein said BCG is a Tice or RIVM strain of bacille Calmette-Guerin (BCG).

4. The method of claim 2, wherein said BCG is administered in a dosage of about $1\times10^5$ to $5\times10^7$ CFU.

5. The method of claim 2, wherein the BCG is administered such that the dosage is distributed at two or more sites.

6. The method of claim 5, where said sites are near the axillary, cervical or inguinal lymph nodes.

7. The method of claim 2, wherein the subject is administered a plurality of doses of the BCG and wherein the doses are at least one day apart.

8. The method of claim 7, wherein the BCG composition is administered twice.

9. The method of claim 8, wherein said doses are at least two weeks apart.

10. The method of claim 7, wherein the dosage of BCG comprised in a given dose is about half of the dosage of BCG comprised in a previous dose.

11. The method of claim 2, further comprising determining whether said subject is PPD positive prior to administering said BCG composition.

12. The method of claim 2, further comprising administering a chemotherapy, a radiotherapy, a gene therapy, an immunotherapy or a surgical therapy.

13. The method of claim 2, wherein the malignant melanoma comprises a TA90 antigen or other tumor glycoprotein.

14. The method of claim 2, further comprising determining the subject's immune response to a cancer antigen.

15. The method of claim 14, further comprising administering at least one additional dose of said BCG composition to subjects that do not have an increased immune response to a cancer antigen following administration of the previous dose of BCG.

16. The method of claim 14, wherein determining the subject's immune response to a cancer antigen is by detection of a cancer antigen specific antibody.

17. The method of claim 14, wherein the cancer specific antigen is the TA90 antigen.

18. The method of claim 2, wherein said BCG composition consists essentially of BCG.

19. A method of determining whether a subject with cancer is responding to BCG immunotherapy in accordance with claim 1 comprising measuring a specific immune response to a cancer antigen in said subject before and after administration of the BCG immunotherapy.

* * * * *

UNITED STATES PATENT AND TRADEMARK OFFICE
CERTIFICATE OF CORRECTION

PATENT NO. : 8,557,257 B2  
APPLICATION NO. : 12/293766  
DATED : October 15, 2013  
INVENTOR(S) : Donald L. Morton Page 1 of 1

It is certified that error appears in the above-identified patent and that said Letters Patent is hereby corrected as shown below:

In item 52 on first page of title page, line 2, "U.S. Cl.", delete "424/92" and insert --424/9.2-- therefor.

In item 56 on first page of title page, "References Cited - U.S. Patent Documents," in respect to U.S. Patent No. 6,090,385, delete "424/179.11" and insert --424/197.11-- therefor.

In item 56 on second page of title page, "References Cited - Other Publications," column two, fifth reference, delete "The immunity" and insert --Tumor immunity-- therefor.

In the Claims:

In claim 4, column 25, line 25, delete "about".

In claim 13, column 26, line 13, before "comprises" insert --tumor--.

Signed and Sealed this  
Fifth Day of August, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,557,257 B2 | Page 1 of 1 |
| APPLICATION NO. | : 12/293766 | |
| DATED | : October 15, 2013 | |
| INVENTOR(S) | : Morton | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1254 days.

Signed and Sealed this
Third Day of March, 2015

Michelle K. Lee
*Deputy Director of the United States Patent and Trademark Office*